US006844353B2

(12) United States Patent
Wedge et al.

(10) Patent No.: US 6,844,353 B2
(45) Date of Patent: Jan. 18, 2005

(54) FUNGICIDAL PROPERTIES OF SAMPANGINE AND ITS ANALOGS TO AGRICULTURALLY IMPORTANT FUNGAL PLANT PATHOGENS

(75) Inventors: David E. Wedge, Oxford, MS (US); Dale G. Nagle, Oxford, MS (US)

(73) Assignees: The United States of America as represented by the Secretary of Agriculture, Washington, DC (US); The University of Mississippi, University, MS (US)

( * ) Notice: Subject to any disclaimer, the term of this patent is extended or adjusted under 35 U.S.C. 154(b) by 127 days.

(21) Appl. No.: 10/400,712

(22) Filed: Mar. 27, 2003

(65) Prior Publication Data

US 2004/0192721 A1 Sep. 30, 2004

(51) Int. Cl.[7] .......................... A01N 43/42; A01N 43/34
(52) U.S. Cl. ...................... 514/280; 514/279; 514/284; 514/285; 514/288
(58) Field of Search ................................. 514/279, 280, 514/284, 285, 288

(56) References Cited

U.S. PATENT DOCUMENTS 5,128,344 A    7/1992   Clark et al.

OTHER PUBLICATIONS

Liu, S. et al., "3–methoxysampangine, a novel antifungal copyrine alkaloid from Cleistopholis patens," Antimicrobial Agents and Chemotherapy, Vo. 34(4), Apr. 1990, pp. 529–533.*
Khan, M.R. et al., "Antimicrobial activity of the alkialoidal constituents of the root bark of eupomatia laurina," Vo. 41 (4), 2003, pp. 277–280.*

* cited by examiner

*Primary Examiner*—John Pak
(74) *Attorney, Agent, or Firm*—John D. Fado; Curtis P. Ribando

(57) ABSTRACT

It has been found that sampangine and related analogs such as benzo[4,5]sampangine, 4-bromosampangine and 4-methoxysampangine may be used as effective fungicidal agents for plants. Fungicidal plant compositions and methods of using the materials for such a purpose are also provided.

8 Claims, No Drawings

FUNGICIDAL PROPERTIES OF SAMPANGINE AND ITS ANALOGS TO AGRICULTURALLY IMPORTANT FUNGAL PLANT PATHOGENS

BACKGROUND OF THE INVENTION

1. Field of the Invention

This invention relates to use of sampagine compounds and related analogs as effective fungicides on plants.

Damage in the United States attributable to serious pathogenic fungi on plants can easily be in the neighborhood of billions of dollars a year. Some of the fungi causing this damage are *Botrytis cinera, Colletotrichum fragariae, C. acutatum, C. gloesporiodes* and *Fusarium oxysporum.*

Chemical resistance to synthetic fungicides is becoming a very serious problem. Effective disease control agents for many crop plant pathogens is becoming limited. While highly diversified in the United States, the $31 billion minor crop industry is of major importance to most states and many rural communities. The United States strawberry crop has an estimated value of well over a billion dollars. Recent studies of *Botrytis* isolates from Louisiana corroborate existing findings that *Botrytis* sp. has developed resistance to benzimidazole and dicarboximide fungicides. It has now been found that sampangine, benzo[4,5]sampangine, 4-bromosampangine, 4-methoxysampangine and structurally related analogs and fractions of plant extract have the ability to be used as a natural product antifungal and post-harvest anti-decay agents.

2. Description of the Prior Art

The closest prior art directed to the use of this class compounds is the patent of Clark et al. U.S. Pat. No. 5,128,344 which teaches mammalian administration of these compounds to control pathological conditions caused by fungal organisms comprising administering the compound in a therapeutically-effective concentration by means of oral, intramuscular, intravenous, or route.

While various methodologies and compositions exist for the use of this class of compounds for fungicidal control in mammals, there remains a need for the creation of improved tools in the area of improved plant fungicides.

Therefore, it is an object of this invention to provide for use of these compounds as fungicides on plants against such organisms such as *Botrytis cinera, Colletotrichum fragariae, C. acutatum, C. gloesporiodes* and *Fusarium oxysporum.*

Yet another object is to provide compositions and methods for the effective control of fungus in plant populations.

SUMMARY OF THE INVENTION

We have discovered that certain sampangine compound and related analogs are effective fungicides for use on plants. The compounds for use in the instant invention are disclosed in U.S. Pat. No. 5,128,344, which is hereby incorporated by reference. Sampangine and related derivatives are taught therein as being useful for preventing or minimizing fungal infections in mammals. Sampangine, benzo[4,5] sampangine, eupolauridine have now been found by means of testing against various plant pathogens to be useful for the control or prevention of various plant diseases including those caused by *Botrytis cinera, Colletotrichum fragariae, C. acutatum, C. gloesporiodes* and *Fusarium oxysporum.*

DETAILED DESCRIPTION OF THE INVENTION

The expression "effective antifungal amount" or variations thereof, is used herein to mean the amount of sampangine or a sampangine derivative which inhibits, at a significant level relative to an untreated control, the propagation and/or growth of a fungal species on a plant which is normally responsible for the attack and decay of the plant, flowers or fruit during growth, storage or marketing. Especially preferred is the amount that will completely inhibit fungal growth (as manifest by the spread of mycelia) under normal conditions of growth or storage, without causing necrotic damage to the plant, flowers or fruit. In general, it is desirable to apply the sampangine or sampangine like compound at concentrations in the range of 0.1 mM to 100 mM, and preferably in a concentration in the range of about 0.2 mM to about 50 mM. The actual target concentration will, of course, depend upon the particular plant, flower or fruit being treated, the species of fungus to be controlled, product formulation and the conditions under which attack and or decay is to be inhibited.

Contemplated for treatment herein are plants having agricultural value such as fruits, vegetables, grains, ornamental stock plants and turf. Berries of commercial interest which are susceptible to fungal decay include, but are not limited to strawberries, raspberries, blueberries, blackberries, gooseberries, hackberries, boysenberries. Vegetables of intended use include, but are not limited to beet, bean, cucurbits, eggplant, pepper and tomato. Fruit of intended use include stone and pome fruit, but are not limited to apple, avocado, pear and grape. The materials are also of use with grains including, but not limited to rice, oats, maize, wheat and barley. The materials are also useful for growth of stock plants and flowers of various species such as, but not limited to, roses, asters, carnations and chrysanthemums.

The fungicide compositions according to the invention typically contain 0.5% to 95% by weight of active material. As described herein, unless otherwise specified, percentages are by weight.

The term "carrier" in the present text, designates an organic or inorganic material, natural or synthetic, with which the active material is combined in order to facilitate its application to the plant, fruit, seeds or soil. This carrier is therefore generally inert and must be agriculturally acceptable, particularly on the treated plant. The carrier may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

The surface-active agent may be an emulsifying, dispersing or wetting agent of the ionic or nonionic type. The following may be mentioned by way of example: polyacrylic acid salts, lignosulphonic acid salts, phenolsulphonic or naphthalenesulphonic acid salts, polycondensates of ethylene oxide and fatty alcohols or fatty acids or fatty amines, substituted phenols (alkylphenols or arylphenols in particular), ester salts of sulphosuccinic acids, taurine derivatives (alkyltaurates in particular), phosphoric esters of alcohols or of polyoxyethylated phenols. The presence of at least one surface-active agent is essential given that the active material and/or the inert carrier are insoluble in water and that the vector agent of the application is water.

These compositions may also contain other ingredients such as, for example, protective colloids, adhesives, thickeners, thixotropic agents, penetrating agents, stabilizers, sequestrants, pigments, colorants and polymers.

More generally, the compositions according to the invention may be combined with all those solid or liquid additives found in the usual formulation procedures.

By way of solid composition forms, the following are included: powders for dusting or dispersing (with a content of active material (i.e. fungicide) which may be as high as 95%) and granules, particularly those obtained by extrusion, by compaction, by impregnation of a granulated carrier and by granulation from a powder (the content of active material in these granules being between 1% and 80% in the latter cases).

By way of liquid composition forms or forms intended to constitute liquid compositions on application, the following are included: solutions, in particular water-soluble concentrates, emulsifiable concentrates, emulsions, concentrated suspensions, aerosols, wettable powders (or spray powder) and pastes.

The emulsifiable or soluble concentrates generally comprise 10% to 80% of active material; the emulsions or solutions ready for application contain, 0.01% to 20% of active material.

For example, in addition to the solvent, the emulsifiable concentrates may contain when necessary, 2% to 20% of appropriate additives such as the stabilizers, surface-active agents, penetrating agents, corrosion inhibitors, colorants or adhesives previously mentioned.

From these concentrates, emulsions of any desired concentration, which are particularly suitable for application to leaves, flowers or fruit may be obtained by dilution with water.

The concentrated suspensions, which can also be applied by spraying, are prepared so as to obtain a stable fluid product which does not form deposits, and they normally contain from 10% to 75% of active material, 0.5% to 15% of surface-active agents, 0.1% to 10% of thixotropic agents, 0% to 10% of appropriate additives, such as pigments, colorants, antifoams, corrosion inhibitors, stabilizers, penetrating agents and adhesives and, by way of carrier, water or an organic liquid in which the active material is barely soluble or insoluble: some organic solid materials or inorganic salts may be dissolved in the carrier to help prevent sedimentation or as anti-freeze for water.

The wettable powders (or spray powders) are normally prepared so that they contain 20% to 95% of active material, and they normally contain, in addition to the solid carrier, from 0% to 5% of a wetting agent, 3% to 10% of a dispersing agent and, when necessary, from 0% to 10% of one or more stabilizers and/or other additives, such as pigments, colorants, penetrating agents, adhesives, or anticoagulating agents, and the like.

To obtain these spray powders or wettable powders, the active materials are thoroughly mixed in appropriate mixers with the additional substances and they are ground using mills or other appropriate grinders. Spray powders are thereby obtained having wettability and ability to form suspensions which are advantageous; they can be suspended in water at any desired concentration and these suspensions may be used very advantageously, in particular for application to plant leaves.

In place of the wettable powders, pastes may be prepared. The conditions and methods for the preparation and the use of these pastes are similar to those for wettable powders or spray powders.

The dispersable granules are normally prepared by agglomeration, in appropriate granulation systems, of the composition of the wettable powder type.

As already indicated, the dispersions and aqueous emulsions (e.g. the compositions obtained by diluting a wettable powder or an emulsifiable concentrate according to the invention with water), are included within the general scope of the present invention. The emulsions may be of the water-in-oil or oil-in-water types and they may have a thick pourable or spreadable consistency like that of a "mayonnaise".

The compositions according to the invention may be used in a preventive or curative capacity for combating fungi, particularly of the basidiomycete, ascomycete, adelomycete or imperfect fungi types, in particular rusts, oidium, eyespot, fusarioses, *Fusarium roseum, Fusarium nivale*, net blotch, leaf blotch, septoria spot, bunt, rhizoctonioses of vegetables and plants in general and, in particular, of cereals such as wheat, barley, rye, oats and their hybrids and also rice and maize.

The compositions according to the invention are active in particular against fungi particularly of the following types: basidiomycetes, ascomycetes, adelomycetes or imperfect fungi such as *Botrytis cinerea, Colletotrichum fragariae, Colletotrichum acutatum, Colletotrichum gloesporiodes, Erysiphe graminis, Puccinia recondita, Piricularia oryzae, Cercospora beticola, Puccinia striiformis, Erysiphe cichoracearum, Fusarium oxysporum* (melonis, for example), *Pyrenophora avenae, Septoria tritici, Venturia inaequalis, Whetzelinia sclerotiorum, Monilia laxa, Mycosphaerella fijiensis, Marssonina panettoniana, Alternaria solani, Aspergillus niger, Cercospora arachidicola, Cladosporium herbarum, Helminthosporium oryzae, Penicillium expansum, Pestalozzia* sp., *Phialophora cinerescens, Phoma betae, Phoma foveata, Phoma lingam, Ustilago maydis, Verticillium dahliae, Ascochyta pisi, Guignardia bidwellii, Corticium rolfsii, Phomopsis viticola, Sclerotinia sclerotiorum, Sclerotinia minor, Coryneum cardinale, Rhizoctonia solani*.

They are also active against the following fungi: *Acrostalagmus koningi, Alternaria, Colletotrichum, Diplodia natalensis, Gaeumannomyces graminis, Gibberella fujikuroi, Hormodendron cladosporioides, Lentinus degener or tigrinus, Lenzites quercina, Memnoniella echinata, Myrothecium verrucaria, Paecylomyces varioti, Pellicularia sasakii, Phellinus megaloporus, Polystictus sanguineus, Poria vaporaria, Sclerotium rolfsii, Stachybotris atra, Stereum, Stilbum* sp., *Trametes trabea, Trichoderma pseudokoningi, Trichothecium roseum*.

The compositions of the invention are particularly useful due to their wide spectrum in relation to cereal diseases (oidium, rust, eyespot, leaf blotch, net blotch, septoria spot and fusarioses). They are also of great interest because of their activity on grey mold (*Botrytis*) and leaf spot, and as a result, they can be applied to products of crop propagation as varied as vines, market garden crops, arboricultural crops and tropical crops such as groundnuts, banana plants, coffee plants, pecan nuts and the like.

In addition to the applications already described above, the compositions according to the invention further possess an excellent biocidal activity towards numerous other varieties of microorganisms amongst which there may be mentioned, without implying a limitation, fungi such as those of the genera:

*Pullularia*, such as the *P. pullulans* species,
*Chaetonium*, such as the *C. globosum* species,
*Aspergillus*, such as the *Aspergillus niger* species,
*Coniophora*, such as the *C. puteana* species.

Because of their biocidal activity, the compositions of the invention make it possible to effectively combat microorganisms whose proliferation creates numerous problems in the agricultural and industrial sectors. To that effect, they are particularly well suited to the protection of plants or industrial products such as timber, leather, paints, paper, rope, plastics and industrial water systems.

The dried ground root bark of *Cleistopholis patens* was percolated initially with n-hexane followed by percolation with 95% ethanol, followed by percolation with hot ethanol. The ethanolic extracts were then combined and subjected to bioassay-directed fractionation by first partitioning between aqueous chloroform followed by aqueous ethyl acetate. The chloroform and ethyl acetate fractions were combined and the combined organic fraction chromatographed over silica gel using chloroform and gradually increasing percentages of methyl alcohol in chloroform as eluents. The methyl alcohol-chloroform fractions were further purified by chromatography over neutral alumina using mixtures of ethyl acetate-n-hexane as eluting solvents.

A compound of the invention was obtained as yellow needles having a melting point of 213°–215°. The needles display a pink fluorescence under long wavelength ultraviolet (UV) irradiation on a silica gel thin layer chromatography (TLC) plate. The molecular formula of the compound determined by electron impact mass spectroscopy (EI-MS) showed a molecular ion peak at m/z 262 corresponding to the molecular formula $C_{16}H_{10}N_2O_2$ which was confirmed by high resolution mass spectroscopy (HR-MS). The molecular formula derived from the high resolution mass spectrum indicated the presence of a condensed ring system. This was verified by the UV spectrum which showed bands at λ max 309, 332 and 409 nm characteristic of a highly conjugated oxoalkaloid. In the proton nuclear magnetic resonance ($^1$H-NMR) spectrum, four of the seven aromatic protons comprised an ABMX system characteristic of a 1,2-disubstituted benzene nucleus. Two pairs of aromatic doublets coupled to each other (δ 9.13 and 8.21) could be assigned to H-2 and H-3 of a pyridine ring. The only remaining signals in the $^1$H NMR were one aromatic proton, resonating as a singlet (δ 8.36) and a three-proton singlet for an aromatic methoxyl at δ 4.18. The $^{13}$C-NMR spectral data revealed sixteen signals as one methoxyl, seven methines and eight quaternary carbons. Based on the $^1$H and $^{13}$C-NMR spectral data, the methoxyl group could be located at either carbons 2, 3, 4 or 5. The location of the methoxyl group at C-3 was established by unambiguous assignment of all of the carbon signals of use of two dimensional nuclear magnetic resonance (2D-NMR) techniques. The structural formula of 3-methoxysampangine is as follows:

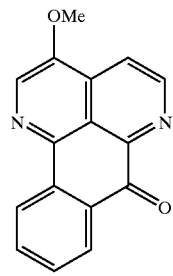

The compound and its analogs were synthesized according to the method shown in Scheme I. Cleistopholine (3) was obtained in a single step (57% yield) through the hetero Diels-Alder reaction of 2-bromo-1,4-naphthoquinone (1) with (E)-2-butenal N,N-dimethylhydrazone (2), followed by in situ elimination of dimethylammonium bromide. The condensation of cleistopholine with dimethylformamide dimethyl acetal provided sampangine (4) in 79% yield. Electrophilic bromination of sampangine with pyridinium bromide perbromide or bromine/pyridine complex delivered exclusively 4-bromosampangine (5, 64%), rather than the anticipated 3-bromo analog. Methanolysis of 4-bromosampangine subsequently led to 4-methoxysampangine (6) in 55% yield. The NMR spectral data for sampangine and 4-methoxysampangine are compared with that for 3-methoxysampangine in Tables I and II. These assignments are based on a careful analysis of the $^1$H, attached proton test (APT), correlated spectroscopy (COSY), and short and long range (J=5 and 10 Hz) heterocorrelated (HETCOR) NMR spectra for each compound. The unambiguous C-7 carbonyl resonance allows for a clear recognition of certain key atoms through HETCOR three-bond connections (e.g. H-8, C-10, etc.) and thence the remaining atoms by correlation with the other spectra. Consistent with these assignments are significant chemical shift changes for C-4, C-5, C-6a, H-3 and H-5 of 4-methoxysampangine and C-2, C-3, C-11b, H-2 and H-4 of 3-methoxysampangine relative to sampangine.

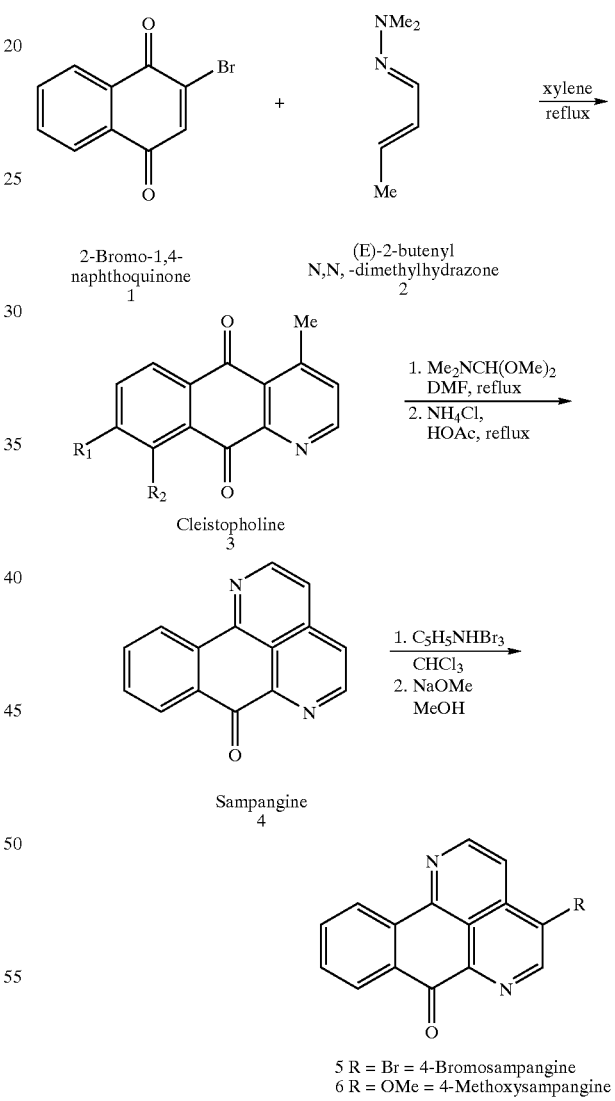

EXAMPLE I

Preparation of 2-bromo-1,4-naphthoquinone (1). A 3-L, three-necked, round-bottomed flask fitted with a mechanical stirrer, a 500 mL addition funnel and a thermometer was charged with glacial acetic acid (500 mL), water (1000 mL) and N-bromosuccinimide (71.2 g, 0.40 mol). The mixture was warmed to 45° C. during which time a yellow solution was obtained. An acetic acid (500 mL) solution of 1-naphthol (14.4 g, 0.10 mol) was then added dropwise over a period of 75 minutes so as to give a red solution, the latter of which was stirred an additional 30 minutes at 45° C. before cooling to room temperature. The resulting mixture was diluted with water (1500 mL) and extracted with methylene chloride (6×400 mL). The combined organic extracts were in turn washed with water (4×400 mL) and saturated sodium bicarbonate solution (4×300 mL). Rotary evaporation of the solvent following drying over magnesium sulfate yielded a yellow solid that was recrystallized from 95% ethanol to yield pure 2-bromo-1,4-naphthoquinone (18.50 g, 78%); mp 130.5°–132° C. (lit. mp 131°–132° C.). IR (KBr) 3050, 1675, 1655, 1585, 1570, 1330, 1310, 1295, 1270, 1245, 1220, 1120, 1060, 910, 890, 820, 790, 775, 670, 665 cm$^{-1}$; $^1$H NMR (CDCl$_3$) δ 8.21–8.14 (m, 1H), 8.11–8.05 (m, 1H), 7.80–7.73 (m, 2H), 7.52 (s, 1H); $^{13}$C NMR (CDCl$_3$) 182.4 (0), 177.8 (0), 140.3 (1), 140.1 (0), 134.4 (1), 134.1 (1), 131.7 (0), 130.9 (0), 127.8 (1), 126.9 (1) ppm.

EXAMPLE II

Preparation of (E)-2-Butenal N,N-Dimethylhydrazone (2). A 250 mL, round-bottomed flask equipped with a 60 mL addition funnel was charged with crotonaldehyde (74.7 mL, 0.90 mol) and cooled in an ice-water bath. 1,1-Dimethylhydrazine (75.3 mL, 0.99 mol) was then added dropwise to the cold aldehyde over a period of 15 minutes. The layers were separated after allowing the reaction to stir at ambient temperature for 45 minutes. The organic layer was dried over calcium chloride, decanted, and distilled through a Vigreaux column. Collection of the fraction boiling at 53°–58° C., 15–18 mm Hg (water aspirator) gave 58.8 g (58%) of pure (E)-2-Butenal N,N-dimethylhydrazone. $^1$NMR (CDCl.sub.3) δ 6.98 (d, J=8.9 Hz, 1H), 6.18 (ddq, J=15.5, 8.9, 1.7 Hz, 1H), 5.78 (dq, J=15.5, 6.8 Hz, 1H), 2.78 (s, 6H), 1.78 (dd, J=6.8, 1.7 Hz, 3H).

EXAMPLE III

Preparation of Cleistopholine (4). (E)-2-Butenal N,N-dimethylhydrazone, (3.70 g, 0.033 mol) in dry xylene (10 mL, Fisher) was added to a xylene solution (50 mL) of 2-bromo-1,4-naphthoquinone, (6.00 g, 0.025 mol) in a 200 mL, round-bottomed flask fitted with a condenser. The dark mixture was then heated at reflux for 6 hours under a nitrogen atmosphere before decanting the solution into a 500 mL separatory funnel. The solids coating the wall of the flask were washed thoroughly with ethyl acetate (6×25 mL) and these washings added to the separatory funnel. The combined organic solutions were extracted with 2N sulfuric acid solution (1×100 mL followed by 2×75 mL). The acid layers were then combined, chilled in ice, and made basic (~pH 10 test paper) with sodium hydroxide before extracting with ethyl acetate (4×100 mL). The latter organic layers were dried over potassium carbonate and concentrated to dryness on a rotary evaporator. This material was applied to a 4×70 cm column of silica gel (Merck 230–400 mesh) and the product eluted with ethyl acetate. Concentration of the appropriate column fractions yielded pure cleistopholine (3.20 g, 57%); mp 202°–204° C. (lit. mp 198°–201° C.). IR (KBr) 1680, 1660, 1590, 1300, 980, 720 cm$^{-1}$; $^1$H NMR (CDCl$_3$) δ 8.86 (d, J=4.9 Hz, 1H), 8.34–8.30 (m, 1H), 8.24–8.19 (m, 1H), 7.82–7.76 (m, 2H), 7.47 (dd, J=4.9, 0.7 Hz, 1H), 2.88 (br s, 3H); $^{13}$C NMR (CDCl$_3$) 184.7 (0), 181.9 (0), 153.4 (1), 151.5 (0), 150.0 (0), 134.5 (1), 134.1 (1), 133.8 (0), 132.5 (0), 131.2 (1), 129.1 (0), 127.3 (1), 127.1 (1), 2.28 (3) ppm.

EXAMPLE IV

Preparation of Sampangine (4). Dimethylformamide dimethyl acetal (1.50 mL, 11.34 mmol, Aldrich) was added to a solution of cleistopholine, (1.95 g, 8.73 mmol) in dimethylformamide (5 mL). The mixture was then heated for 30 minutes by submerging the reaction vessel into an oil bath preheated to 120° C. At this point, ammonium chloride (4.5 g) and glacial acetic acid (15 mL) were added to the reaction and the heating (120° C.) continued for an additional 30 minutes. After allowing to cool, the reaction was poured onto water (200 mL) and partitioned with methylene chloride (5×100 mL). The combined organic phases were washed with saturated sodium bicarbonate solution (3×100 mL), water (3×100 mL), dried over potassium carbonate, and concentrated to dryness. The residual dark brown solids were chromatographed on silica gel (4×70 cm column, Merck 230–400 mesh) while eluting with ethyl acetate. Concentration of the appropriate column fractions provided pure sampangine (1.60 g, 79%), mp 220–222 (lit. mp 216°–218° C.). IR 1670, 1615, 1590, 1400, 1380, 1320, 1275, 1225, 760, 725 cm$^{-1}$; $^1$H and $^{13}$C NMR (see Tables I and II).

TABLE I $^1$H NMR DATA FOR SAMPANGINE, 4-METHOXYSAMPANGINE AND 3-METHOXYSAMPANGINE

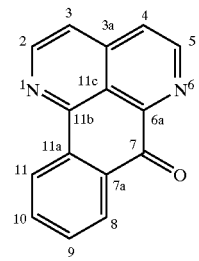

Chemical Shift, ppm (CDCl$_3$)

| Pos | sampangine (4) | 4-methoxysampangine (6) | 3-methoxysampangine |
|---|---|---|---|
| 2 | 8.88(d, J=5.8Hz, 1H) | 8.89(d, J=5.8Hz, 1H) | 8.36(s, 1H) |
| 3 | 7.71(d, J=5.8Hz, 1H) | 8.00(d, J=5.8Hz, 1H) | — |
| 3a | — | — | — |

TABLE I-continued

¹H NMR DATA FOR SAMPANGINE, 4-METHOXYSAMPANGINE AND 3-METHOXYSAMPANGINE

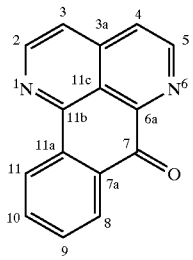

Chemical Shift, ppm (CDCl₃)

| Pos | sampangine (4) | 4-methoxysampangine (6) | 3-methoxysampangine |
|---|---|---|---|
| 4 | 7.92(d, J=5.5Hz, 1H) | — | 8.21(d, J=5.4Hz, 1H) |
| 5 | 9.13(d, J=5.5Hz, 1H) | 8.66(s, 1H) | 9.13(d, J=5.4Hz, 1H) |
| 6a | — | — | — |
| 7 | — | — | — |
| 7a | — | — | — |
| 8 | 8.46(dd, J=7.8, 1.2Hz, 1H) | 8.49(dd, J=7.9, 1.2Hz, 1H) | 8.43(dd, J=7.8, 1.2Hz, 1H) |
| 9 | 7.69(ddd, J=7.8, 7.8, 1.2Hz, 1H) | 7.69(ddd, J=7.9, 9, 1.2Hz, 1H) | 7.61(ddd, J=7.8, 7.8, 1.2Hz, 1H) |
| 10 | 7.83(ddd, J=7.8, 7.8, 1.2Hz, 1H) | 7.82(ddd, J=7.9, 7.9, 1.2 Hz, 1H | 7.78(ddd, J=7.8, 7.8, 1.2Hz, 1H) |
| 11 | 8.82(dd, J=7.8, 1.2, 1H) | 8.85(dd, J=7.9, 1.2Hz, 1H | 8.65(dd, J=7.8, 1.2Hz, 1H) |
| 11a | — | — | — |
| 11b | — | — | — |
| 11c | — | — | — |
| OCH₃ | — | 4.25(s, 3H) | 4.18(s, 3H) |

TABLE II

¹³C NMR DATA FOR SAMPANGINE, 4-METHOXYSAMPANGINE AND 3-METHOXYSAMPANGINE

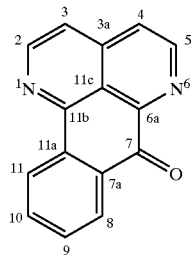

Chemical Shift (CDCl₃)

| Pos | sampangine (4) | 4-methoxysampangine (6) | 3-methoxysampangine |
|---|---|---|---|
| 2 | 147.1 (1) | 146.6 (1) | 126.8 (1) |
| 3 | 118.9 (1) | 114.3 (1) | 149.9 (0) |
| 3a | 138.3 (0) | 130.3 (0) | 131.8 (0) |
| 4 | 123.2 (1) | 152.7 (0) | 118.8 (1) |
| 5 | 148.2 (1) | 128.9 (1) | 148.0 (1) |
| 6a | 147.5 (0) | 141.0 (0) | 147.2 (0) |
| 7 | 181.5 (0) | 181.1 (0) | 182.0 (0) |
| 7a | 132.0 (0) | 132.8 (0) | 131.5 (0) |
| 8 | 128.1 (1) | 128.4 (1) | 128.5 (1) |
| 9 | 131.1 (1) | 131.2 (1) | 130.2 (1) |
| 10 | 134.4 (1) | 134.2 (1) | 134.6 (1) |
| 11 | 125.1 (1) | 125.3 (1) | 124.6 (1) |
| 11a | 135.0 (0) | 135.6 (0) | 135.7 (0) |
| 11b | 150.7 (0) | 150.4 (0) | 143.2 (0) |

TABLE II-continued

¹³C NMR DATA FOR SAMPANGINE, 4-METHOXYSAMPANGINE AND 3-METHOXYSAMPANGINE

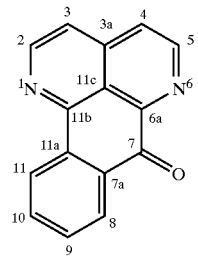

Chemical Shift (CDCl₃)

| Pos | sampangine (4) | 4-methoxysampangine (6) | 3-methoxysampangine |
|---|---|---|---|
| 11c | 119.3 (0) | 120.0 (0) | 119.7 (0) |
| OCH₃ | — | 56.9 (3) | 56.6 (3) |

EXAMPLE V

Preparation of 4-bromosampangine (5). A mixture of pyridinium bromide perbromide (390 mg, 1.2 mmol) and sampangine, (232 mg, 1.0 mmol) in chloroform (12 mL) was heated at reflux for 15 hours. Saturated sodium bicarbonate solution (100 mL) was added to the cooled reaction and the mixture stirred vigorously for 30 minutes. The two layers were separated and the aqueous phase extracted with chloroform (2×30 mL). The combined organic layers were dried over potassium carbonate and concentrated to dryness. The residual solid was applied to a 2×40 cm column of silica gel (Merck 230–400 mesh) and the pure product (200 mg, 64%) eluted with chloroform, mp 180° C. dec. IR (KBr) 1670, 1590, 1400, 1320, 1310, 1275, 1230, 980, 790, 755, 720 cm$^{-1}$; $^1$H NMR (CDCl$_3$) δ 9.28 (s, 1H), 8.99 (d, J=5.9 Hz, 1H), 8.85 (dd, J=7.9, 1.4 Hz, 1H), 8.46 (dd, J=7.9, 1.4 Hz, 1H), 7.96 (d, J=5.9 Hz, 1H), 7.86 (ddd, J=7.7, 7.9, 1.4 Hz, 1H), 7.72 (ddd, J=7.9, 7.9, 1.4 Hz, 1H); $^{13}$C NMR (CDCl3) 181.6 (0), 151.7 (0), 150.2 (1), 148.6 (1), 146.7 (0), 138.6 (0), 135.1 (0), 135.0 (1), 132.3 (0), 131.8 (1), 128.7 (1), 125.8 (1), 123.7 (0), 120.5 (0), 118.3 (1) ppm; HR MS calc. for C$_{15}$H$_7$BrN$_2$O 309.9741, found 309.9747.

EXAMPLE VI

Preparation of 4-methoxysampangine (6). A dry methanol (6 mL) solution of sodium methoxide (80 mg, 1.48 mmol) and 4-bromosampangine (80 mg, 0.26 mmol) was heated to reflux for 20 hours. The cooled solution was transferred to a separatory funnel, diluted with chloroform (50 mL), and washed with water (2×60 mL). The chloroform layer was subsequently dried over potassium carbonate and concentrated to dryness. TLC analysis of the residue (silica gel, ethyl acetate eluant) revealed only one spot R$_f$=0.15) that was substantially more polar than 4-methoxysampangine. Chromatography of this residue on silica gel (1×25 cm column, Merck 230-400 mesh) while eluting with ethyl acetate-methanol (4:1) provided pure 4-methoxysampangine (37 mg, 55%), mp 258° C. dec. IR (KBr) 1670, 1595, 1570, 1500, 1405, 1375, 1320, 1295, 1240, 1100, 1040, 1030, 985, 920, 790, 720, 615 cm$^{-1}$; $^1$H and $^{13}$C NMR (see Tables I and II).

EXAMPLE VII

Preparation of benzo[4,5]sampangine (9). As illustrated in Scheme II, a suspension of 4.47 g (0.03 mol) of 1,4-naphthoquinone (7) in 600 ml of absolute ethanol, containing 3.37 g (0.03 mol) of 1-aminoacetophenone (8) and 1.66 g (0.003 mol) of cerium trichloride heptahydrate was warmed to dissolve, then allowed to stand at room temperature and a steady current of air was continuously blown into the reaction mixture for 24 hours. A red precipitate was formed and collected by filtration, then washed with a small amount of absolute ethanol. The filtrate was repeated above procedure twice, and a total of 7.26 g (60.4%) of 2-[o-acetyl]-anilino-1,4-naphthoquinone (9) was obtained as red needles, mp. 177°–179° C. EIMS m/z 291 (M$^+$), $^1$H-nmr, δ (CDCl$_3$) 2.66 (3H, s), 6.99 (1H, s) 7.06 (1H, d, J=9.0 Hz), 7.14 (1H, ddd, J=6.0, 6.0, 1.0 Hz), 7.55 (1H, ddd, J=9.0, 6.0, 1.0 Hz), 7.65 (1H, ddd, J=8.0, 8.0, 1.5 Hz), 7.73 (1H, ddd, J=8.0, 8.0, 1.5 Hz), 7.93 (1H, dd, J=6.0, 1.0 Hz), 8.05 (1H, dd, J=9.0, 1.0 Hz), 8.13 (1H, dd, J=9.0, 1.0 Hz).

Scheme II

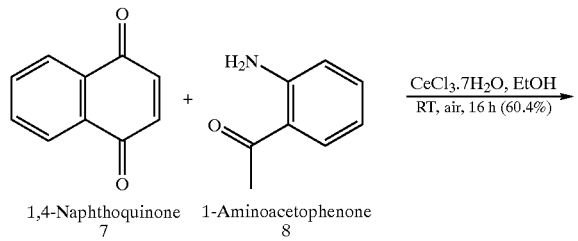

1,4-Naphthoquinone 7

1-Aminoacetophenone 8

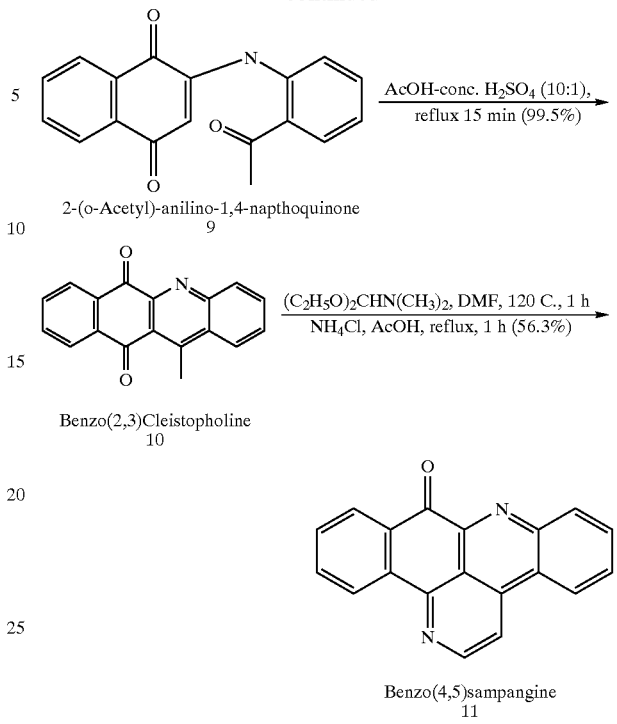

2-(o-Acetyl)-anilino-1,4-napthoquinone 9

Benzo(2,3)Cleistopholine 10

Benzo(4,5)sampangine 11

To a cold, stirred suspension of 4 g (15.7 m mols) of 2-[o-acetyl]-anilino-1,4-naphthoquinone (9) in 13.2 mL of glacial acetic acid was slowly added. 13.2 ml of concentrated H$_2$SO$_4$. The reaction mixture was then gently refluxed for 15 minutes, cooled, and poured into 2 liters of ice-H$_2$O. The yellow precipitate was collected and washed with a small amount of ice cold ice-H$_2$O to give 3.23 g (99.5%) of dirty greenish yellow fine needles of Benzo[2,3]cleistopholine (10) mp. 237°–239° (d). EIMS M/z 273 (M$^+$), IRυ$_{max}$ (KBr) 1680, 1655, 1590, 1495, 1375, 1260, 1080, 943, 770, 720 cm$^{-1}$; $^1$H-nmr, δ (CDCl$_3$) 3.22 (3H, s, CH$_3$-13), 7.69 (1 H, ddd, J=6.7, 6.7, 1.3 Hz), 7.70 (1H, m), 7.78 (1H, m), 7.84 (1H, ddd, J=6.7, 6.7, 1.3 Hz), 8.25 (1H, dd, J=6.0, 2.5 Hz), 8.29 (1H, brd, J=6.7 Hz), 8.34 (1H, dd, J=6.0, 2.5 Hz), 8.39 (1H, brd, J=6.7 Hz).

A suspension of 2.38 g (8.73 m mol) of Benzo[2,3]cleistopholine in 3 ml of DMF and 1.67 g of dimethyl formamide-diethylacetal was stirred under N$_2$ and heated at 120° C. for 1 hour. The reaction mixture was cooled and 15 ml of glacial acetic acid and 4.5 g of NH$_4$Cl was added carefully and the reaction mixture was refluxed for another hour. Water (300 ml) was added to the reaction mixture, followed by extraction with CH$_2$Cl$_2$ (150 ml×4). The total organic layer was washed with 150 ml of saturated NaHCO$_3$ cosolution, then with 150 ml of H$_2$O, and dried over anhydrous K$_2$CO$_3$. After removal of solvent, the resulting residue was chromatographed over silica gel (400 g) and eluted with ethyl acetate to give 1.824 (56.3%) of benzo[4,5]sampangine (11), as bright yellow needles, mp. 260°–262° C. EIMS m/z 282 (M$^+$), IRυ$_{max}$ (KBr) 1680, 1590, 1442, 1390, 1300, 1262, 1060, 950, 767, 740 cm$^{-1}$, $^1$H and $^{13}$C NMR (see Table III).

TABLE III

$^1$H and $^{13}$C NMR DATA FOR BENZO[4,5]SAMPANGINE

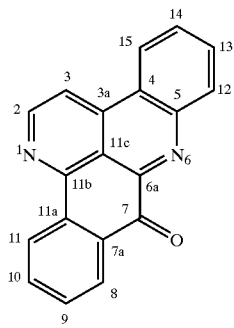

| Pos | $^1$H NMR | $^{13}$C NMR |
|---|---|---|
| 2 | 8.97(d, J=5.7Hz, 1H) | 148.9 (1) |
| 3 | 8.30(d, J=5.7Hz, 1H) | 115.5 (1) |
| 3a | — | 137.8 (0) |
| 4 | — | 123.5 (0) |
| 5 | — | 145.8 (0) |
| 6a | — | 146.0 (0) |
| 7 | — | 182.2 (0) |
| 7a | — | 132.5 (0) |
| 8 | 8.44(dd, J=7.8, 1.0Hz, 1H) | 128.7 (1) |
| 9 | 7.66(ddd, J=7.8, 7.4, 1.0Hz, 1H) | 131.2 (1) |
| 10 | 7.80(ddd, J=7.8, 7.4, 1.0Hz, 1H) | 134.9 (1) |
| 11 | 8.79(dd, J=7.8, 1.0Hz, 1H) | 125.8 (1) |
| 11a | — | 136.1 (0) |
| 11b | — | 150.5 (0) |
| 11c | — | 117.0 (0) |
| 12 | 8.55(dd, J=7.1, 1.4Hz, 1H) | 133.1 (1) |
| 13 | 7.93(ddd, J=7.1, 7.0, 1.4Hz, 1H) | 131.6 (1) |
| 14 | 7.84(ddd, J=7.1, 7.0, 1.4Hz, 1H) | 130.3 (1) |
| 15 | 8.55(dd, J=7.1, 1.4Hz, 1H) | 122.9 (1) |

Antifungal Methods

Pathogen production. Isolates of *Colletotrichum acutatum* Simmonds, *Colletotrichum fragariae* Brooks, and *Colletotrichum gloeosporioides* (Penz.) Penz. & Sacc. in Penz. were obtained from B. J. Smith, USDA, ARS, Small Fruit Research Station, Poplarville, Miss. *Colletotrichum fragariae* (isolate CF63), *C. acutatum* (isolate CAGoff), and *C. gloeosporioides* (isolate CG162) were used for all pathogen and bioautography studies. Isolate CF63 is one of the most virulent isolates at infecting strawberry plants and inducing both crown and fruit rot (Smith and Black, 1990). CF63, CAGoff, and CG162 were used as standard test isolates because of our extensive knowledge of these isolates and their known fungicide sensitivity profiles in both bioautography and microtiter formats. The three *Colletotrichum* species were isolated from strawberry (*Fragaria x ananassa* Duchesne). *Botrytis cinerea* Pers.: Fr, was isolated from commercial grape (*Vitis vinifera* L.) and *Fusarium oxysporum* Schlechtend: Fr from orchid (*Cynoches* sp.). *Phomopsis viticola* (Sacc.) and *P. obscurans* (Ellis & Everh.) Sutton were from Mike A. Ellis, Ohio State University, Wooster, Ohio. Fungi were grown on potato-dextrose agar (PDA, Difco, Detroit, Mich.) in 9 cm petri dishes and incubated in a growth chamber at 24±2° C. and under cool-white fluorescent lights (55±5 mmols·m$^{-2}$·sec$^{-1}$ light) with 12 hour photoperiod.

Inoculum preparation. Conidia were harvested from 7–10 day-old cultures by flooding plates with 5 mL of sterile distilled water and dislodging conidia by softly brushing the colonies with an L-shaped glass rod. Conidial suspensions were filtered through sterile miracloth (Calbiochem-Novabiochem Corp., La Jolla, Calif.) to remove mycelia. Conidia concentrations were determined photometrically, from a standard curve based on the percent of transmittance (% T) at 625 nm and suspensions were then adjusted with sterile distilled water to a concentration of 1.0×10$^6$ conidia/mL.

Bioautography: Extracts containing antifungal compounds were indicated by clear zones of fungal growth inhibition directly on chromatographic plates using modifications of thin layer chromatography (TLC) bioautographic assays (Homans & Fuchs, 1970; Osborne, et al., 1994; Wedge and Nagle, 2000). Extracts were dissolved as described above. Using a disposable glass micro pipette for each sample, 4 μL of each test extract was placed on the TLC plate and chromatographed in one-dimension.

To detect biological activity directly on the TLC plate, silica gel plates were sprayed with either of the three spore suspensions adjusted to a final concentration of 3.0×10$^5$ conidia/mL with liquid potato-dextrose broth (PDB, Difco, Detroit, Mich.) and 0.1% Tween-80. Using a 50 mL chromatographic sprayer, each glass silica gel thin layer chromatography (TLC) plates with a fluorescent indicator (250 μm, Silica Gel GF Uniplate, Analtech, Inc. Newark, Del.) was sprayed lightly (to a damp appearance) three times with the conidial suspension. Inoculated plates were then placed in a 30×13×7.5 cm moisture chamber (398-C, Pioneer Plastics, Inc. Dixon, Ky.) and incubated in a growth chamber at 24±1° C. and 12 hour photoperiod under 60±5 mmols·m$^{-2}$·sec$^{-1}$ light. Inhibition of fungal growth was measured 4 days after treatment. Sensitivity of each fungal species to each test compound was determined by comparing size of inhibitory zones.

Microtiter assay. A standardized 96-well microtiter plate assay developed for discovery of natural product fungicidal agents was used to evaluate naturally occurring antifungal agents from *Macaranga monanara*. A 96-well microtiter assay was used to determine sensitivity of *B. cinerea, C. acutatum, C. fragariae, C. gloeosporioides, F. oxysporum, Phomopsis viticola*, and *P. obscurans* to the various antifungal agents in comparison with known fungicidal standards. Vinclozolin, captan, and thiabendazole, which represent three different modes of action, were used as standards in this experiment. Each fungus was challenged in a dose-response format using test compounds where the final treatment concentrations were 0.3, 3.0 and 30.0 μM. Microtiter plates (Nunc MicroWell, untreated; Roskilde, Denmark) were covered with a plastic lid and incubated in a growth chamber as described previously for fungal growth. Growth was then evaluated by measuring absorbance of each well at 620 nm using a microplate photometer (Packard Spectra Count, Packard Instrument Co., Downers Grove, Ill.). Each fungus was challenged in a dose-response format using test compounds where the final treatment concentrations were 0.3, 3.0 and 30.0 μM. Microtiter plates (Nunc MicroWell, untreated; Roskilde, Denmark) were covered with a plastic lid and incubated in a growth chamber at 24±1° C. and 12 hour photoperiod under 60±5 μmol light. Growth was then evaluated by measuring absorbance of each well at 620 nm using a microplate photometer (Packard Spectra Count, Packard Instrument Co., Downers Grove, Ill.).

Microbioassy Experimental Design. Chemical sensitivity each of *B. cinerea, C. acutatum, C. fragariae, C. gloeosporiodes, F. oxysporum, Phomopsis viticola*, and *P. obscurans* was evaluated using 96-well plate microbioassay format. Each chemical was evaluated in duplicate at each dose (0.3, 3.0 and 30.0 μM). Sixteen wells containing broth and inoculum served as positive controls, eight well containing solvent at the appropriate concentration and broth without inoculum were used as negative controls. Mean absorbance values and standard errors were used to evaluate fungal growth at 46 hours and 72 hours except for *P. obscurans* and *P. viticola*. The data were recorded at 120 hours. Analysis of variance of means for percent inhibition of each fungus at each dose of test compound (n=4) relative to the untreated positive growth controls (n=32) were used to evaluate fungal growth inhibition. Treatments were arranged as a split-plot design replicated twice in time. Whole-plots were fungal isolates and sub-plots were chemicals. Each dose level and response time was analyzed separately. The SAS system's analysis of variance procedure (Statistical Analysis System, Cary, N.C.) was used to identify significant factors and Fisher's protected LSD was used to separate means. The results of these tests are shown below.

SAMPANGINE

Percent inhibition–Percent Stimulation±SEM

TABLE IV

| | 0.3 μM | | 3.0 μM | | 30 μM | |
|---|---|---|---|---|---|---|
| *F. oxysporum* | 48 hrs | 72 hrs | 48 hrs | 72 hrs | 48 hrs | 72 hrs |
| Captan | −2.8 ± 4.7 | 4.7 ± 2.1 | −77.2 ± 7.2 | −24.1 ± 6.5 | −100.0 ± 0.4 | −99.8 ± 0.2 |
| Sampangine | −14.7 ± 4.4 | −4.9 ± 2.3 | −86.6 ± 2.8 | −42.9 ± 3.1 | −100.0 ± 0.4 | −100.0 ± 0.4 |
| BAS 490 | −82.3 ± 3.0 | −30.3 ± 6.9 | −92.7 ± 0.6 | −65.5 ± 1.6 | −94.7 ± 0.5 | −69.5 ± 2.0 |
| Fenhexamid | −3.0 ± 4.4 | 0.1 ± 2.8 | −15.3 ± 1.7 | −3.7 ± 2.6 | −28.5 ± 1.3 | −21.2 ± 2.1 |
| Iprodione | −1.8 ± 2.6 | 2.3 ± 3.0 | −8.3 ± 3.1 | 4.1 ± 4.0 | −7.7 ± 4.6 | 11.2 ± 5.3 |
| Benomyl | −3.3 ± 4.7 | 1.6 ± 3.2 | −12.0 ± 3.0 | −0.8 ± 3.5 | −86.3 ± 1.6 | −77.2 ± 2.3 |
| Fenbucanazole | −15.3 ± 2.6 | −10.4 ± 2.7 | −33.1 ± 4.2 | −29.3 ± 2.6 | −45.5 ± 3.4 | −44.5 ± 2.5 |
| Cyprodinil | 5.4 ± 4.8 | 5.1 ± 2.8 | −16.9 ± 5.5 | −6.2 ± 2.5 | −69.1 ± 4.6 | −31.3 ± 4.9 |
| 4-bromo sampangine | −20.4 ± 4.6 | −2.8 ± 1.9 | −42.3 ± 4.5 | −14.0 ± 2.1 | −25.8 ± 2.6 | −9.1 ± 3.0 |
| 4-meth oxysampangine | −10.3 ± 4.7 | 2.9 ± 4.2 | −66.8 ± 5.5 | −33.5 ± 1.9 | −43.6 ± 2.7 | −23.5 ± 1.6 |
| Benzo[4,5] sampangine | −48.2 ± 4.4 | −17.1 ± 2.0 | −77.7 ± 5.7 | −27.2 ± 6.2 | −57.9 ± 3.2 | −27.2 ± 1.9 |

TABLE V

| | 0.3 μM | | 3.0 μM | | 30 μM | |
|---|---|---|---|---|---|---|
| *C. gloeosporioides* | 48 hrs | 72 hrs | 48 hrs | 72 hrs | 48 hrs | 72 hrs |
| Captan | 4.4 ± 4.4 | 15.3 ± 2.1 | −96.3 ± 2.1 | −97.9 ± 0.7 | −99.7 ± 0.6 | −100.0 ± 0.3 |
| Sampangine | −63.8 ± 8.6 | −32.9 ± 8.3 | −98.3 ± 0.6 | −98.8 ± 0.4 | −99.2 ± 0.8 | −99.7 ± 0.4 |
| BAS 490 | −83.3 ± 3.2 | −58.7 ± 5.0 | −92.4 ± 1.5 | −82.6 ± 3.4 | −97.5 ± 1.0 | −89.7 ± 1.9 |
| Fenhexamid | 21.6 ± 9.0 | 11.3 ± 5.5 | 32.5 ± 6.4 | 16 ± 2.0 | 0.3 ± 3.0 | −6.5 ± 4.2 |
| Iprodione | 33.4 ± 10.1 | 17.5 ± 6.7 | 49.6 ± 8.4 | 30.7 ± 4.0 | −23.4 ± 9.1 | 17.4 ± 7.9 |
| Benomyl | −47.5 ± 9.2 | −16.1 ± 6.5 | −84.2 ± 3.8 | −59.9 ± 9.6 | −82.4 ± 4.0 | −44.8 ± 8.6 |
| Fenbucanazole | −86.1 ± 1.4 | −59.1 ± 3.6 | −95.0 ± 1.1 | −98.1 ± 0.4 | −99.0 ± 0.7 | −99.6 ± 0.2 |
| Cyprodinil | −84.3 ± 2.3 | −55.7 ± 4.6 | −91.3 ± 1.3 | −83.7 ± 1.8 | −91.1 ± 7.0 | −93.0 ± 0.4 |
| 4-bromo sampangine | −100.0 ± 1.5 | −99.0 ± 0.6 | −98.9 ± 0.5 | −99.1 ± 0.4 | −96.0 ± 1.4 | −99.7 ± 0.4 |
| 4-meth oxysampangine | −48.5 ± 6.7 | −15.6 ± 1.9 | −94.4 ± 0.9 | −91.1 ± 2.1 | −95.9 ± 3.4 | −79.7 ± 6.0 |
| Benzo[4,5] sampangine | −100.0 ± 1.0 | −100.0 ± 0.3 | −98.6 ± 1.1 | −99.7 ± 0.4 | −100.0 ± 1.8 | −100.0 ± 0.9 |

TABLE VI

| | 0.3 μM | | 3.0 μM | | 30 μM | |
|---|---|---|---|---|---|---|
| *C. fragariae* | 48 hrs | 72 hrs | 48 hrs | 72 hrs | 48 hrs | 72 hrs |
| Captan | 20.5 ± 9.5 | 14.9 ± 2.2 | −98.1 ± 0.6 | −97.8 ± 1.6 | −98.8 ± 0.8 | −99.5 ± 0.3 |
| Sampangine | −55.7 ± 4.5 | −32.6 ± 5.0 | −96.9 ± 0.8 | −96.8 ± 0.4 | −99.6 ± 0.9 | −100.0 ± 0.4 |
| BAS 490 | −68.8 ± 7.1 | −35.6 ± 5.6 | −86.4 ± 3.5 | −71.9 ± 3.5 | −91.5 ± 1.7 | −80.4 ± 1.4 |
| Fenhexamid | 30.2 ± 10.0 | 12.0 ± 6.7 | 13.6 ± 6.3 | 9.9 ± 4.3 | −19.9 ± 3.4 | −19.5 ± 5.4 |
| Iprodione | 36.4 ± 12.3 | 17.1 ± 3.6 | 42.6 ± 10.4 | 24.0 ± 4.6 | 63.2 ± 10.7 | 57.7 ± 12.0 |
| Benomyl | −51.5 ± 5.0 | −36.8 ± 4.4 | −89.6 ± 1.2 | −92.7 ± 1.0 | −92.4 ± 1.1 | −94.3 ± 0.9 |
| Fenbucanazole | −26.8 ± 14.1 | 19.0 ± 7.7 | −37.0 ± 15.3 | 4.7 ± 4.2 | −99.3 ± 1.1 | −97.7 ± 0.6 |
| Cyprodinil | −98.0 ± 1.6 | −82.6 ± 6.2 | −91.3 ± 1.3 | −83.7 ± 1.8 | −91.1 ± 7.0 | −93.0 ± 0.4 |
| 4-bromo sampangine | −46.3 ± 5.0 | −15.2 ± 8.2 | −87.3 ± 2.0 | −45.8 ± 5.6 | −55.9 ± 7.1 | −26.7 ± 7.3 |
| 4-meth oxysampangine | −15.0 ± 7.5 | −30.2 ± 7.4 | −75.2 ± 6.7 | −44.3 ± 6.5 | −67.9 ± 13.6 | −39.6 ± 6.3 |
| Benzo[4,5] sampangine | −38.4 ± 6.1 | −19.8 ± 7.7 | −72.4 ± 8.5 | −54.7 ± 11.2 | −52.9 ± 6.5 | −29.4 ± 6.8 |

TABLE VII

| C. acutatum | 0.3 μM | | 3.0 μM | | 30 μM | |
|---|---|---|---|---|---|---|
| | 48 hrs | 72 hrs | 48 hrs | 72 hrs | 48 hrs | 72 hrs |
| Captan | 2.7 ± 2.4 | 9.5 ± 1.5 | −98.8 ± 0.4 | −94.8 ± 0.2 | −99.5 ± 0.3 | −99.6 ± 0.2 |
| Sampangine | −13.6 ± 5.8 | −6.0 ± 5.1 | −96.8 ± 0.5 | 6.2 ± 3.8 | −100.0 ± 0.6 | −100.0 ± 0.2 |
| BAS 490 | −63.9 ± 3.8 | −17.8 ± 3.5 | −93.1 ± 0.6 | 14.7 ± 2.5 | −95.1 ± 0.7 | −69.9 ± 2.6 |
| Fenhexamid | 21.6 ± 6.7 | 20.4 ± 5.6 | 6.5 ± 4.9 | 21.8 ± 4.3 | −13.8 ± 5.3 | −1.5 ± 6.7 |
| Iprodione | 26.4 ± 10.7 | 26.8 ± 9.9 | 18.1 ± 3.2 | 10.7 ± 3.1 | 27.9 ± 5.5 | 64.8 ± 4.0 |
| Benomyl | −24.6 ± 6.1 | 7.7 ± 6.6 | −20.3 ± 4.8 | −47.7 ± 4.1 | −16.6 ± 6.3 | 15.2 ± 3.7 |
| Fenbucanazole | 13.0 ± 5.8 | 16.3 ± 5.4 | −3.8 ± 4.8 | −89.9 ± 6.8 | −39.2 ± 3.3 | −21.7 ± 5.8 |
| Cyprodinil | −99.8 ± 0.2 | −85.1 ± 4.3 | −98.6 ± 0.6 | −99.3 ± 2.2 | −98.7 ± 0.5 | −97.9 ± 0.3 |
| 4-bromo sampangine | −23.3 ± 8.0 | −7.1 ± 6.3 | −73.4 ± 6.8 | −24.9 ± 8.7 | −33.4 ± 6.9 | −10.5 ± 6.7 |
| 4-meth oxysampangine | −5.1 ± 7.8 | −0.3 ± 6.4 | −75.1 ± 6.8 | −44.1 ± 6.5 | −51.3 ± 6.2 | −25.4 ± 5.4 |
| Benzo[4,5] sampangine | −30.5 ± 10.2 | −25.9 ± 8.0 | −74.2 ± 6.3 | −46.2 ± 5.2 | −57.0 ± 10.0 | −38.9 ± 5.2 |

TABLE VIII

| B. cinerea | 0.3 μM | | 3.0 μM | | 30 μM | |
|---|---|---|---|---|---|---|
| | 48 hrs | 72 hrs | 48 hrs | 72 hrs | 48 hrs | 72 hrs |
| Captan | 55.9 ± 24.7 | −40.7 ± 16.3 | −38.4 ± 23.5 | −54.6 ± 22.9 | −58.0 ± 23.2 | −54.0 ± 17.9 |
| Sampangine | −27.2 ± 18.6 | −37.0 ± 21.8 | −29.7 ± 24.8 | −40.1 ± 20.6 | −36.9 ± 26.7 | −47.5 ± 27.1 |
| BAS 490 | −71.3 ± 28.0 | −66.6 ± 21.5 | −24.0 ± 32.0 | −37.2 ± 20.2 | −60.1 ± 32.9 | −40.9 ± 17.6 |
| Fenhexamid | −82.9 ± 31.5 | −71.4 ± 24.7 | −34.2 ± 29.1 | −42.7 ± 20.6 | −49.2 ± 32.1 | −40.9 ± 22.6 |
| Iprodione | 10.4 ± 11.1 | −28.3 ± 27.9 | −34.2 ± 29.1 | −43.3 ± 20.5 | −38.1 ± 29.3 | −41.3 ± 20.6 |
| Benomyl | −50.0 ± 26.9 | −71.2 ± 25.1 | −21.6 ± 27.3 | −40.9 ± 22.0 | −39.9 ± 20.4 | −47.3 ± 14.9 |
| Fenbucanazole | −46.0 ± 34.2 | −49.6 ± 24.7 | −35.9 ± 28.3 | −47.0 ± 23.0 | 17.6 ± 52.2 | −29.9 ± 24.2 |
| Cyprodinil | −75.3 ± 21.0 | −61.3 ± 24.4 | −29.4 ± 31.3 | −51.3 ± 30.0 | −2.5 ± 31.6 | −27.3 ± 28.2 |
| 4-bromo sampangine | −41.1 ± 9.4 | −22.6 ± 13.7 | −59.2 ± 6.7 | −38.8 ± 9.4 | −29.7 ± 9.7 | 2.5 ± 8.9 |
| 4-meth oxysampangine | −23.0 ± 14.4 | −4.8 ± 12.6 | −59.2 ± 6.7 | −18.4 ± 5.4 | −20.3 ± 21.8 | 19.0 ± 14.3 |
| Benzo[4,5] sampangine | −70.2 ± 5.8 | −55.2 ± 8.1 | −78.0 ± 3.6 | −46.7 ± 10.2 | −99.2 ± 19.4 | −22.8 ± 14.7 |

EXAMPLE VIII

Protocol for Detached Strawberry Leaf Assay

Strawberry plants of the cultivar Chandler were maintained in a warm greenhouse under conditions suitable for optimum vegetative growth. The youngest fully expanded leaf with the entire petiole from each plant was collected. The petiole of each leaf was inserted into a small test tube (10×4 mm) and filled with sterile distilled water. The left leaflet of each leaf was inoculated with C. fragariae isolate CF-75 (1.5×10$^6$ conidia/ml) using a hand pump sprayer. The inoculated leaves were placed in a dew chamber and incubated overnight at 30° C. and 100% relative humidity, removed from the dew chamber and allowed to dry. The test compound was applied using a chromatography sprayer until the upper surface of each leaflet was coated. After allowing the leaves to air dry for 2 hours, the right leaflet of each leaf was inoculated with C. fragariae isolate CF-75. The leaves were incubated in the dew chamber at 30° C. and 100% relative humidity for 48 hours. The leaves were then removed from the dew chamber and held in a moist chamber for 3 days (total of five days since test compounds were applied). The number of lesions on each leaflet were then counted. The results are shown in Table, below.

TABLE IX[a]

| Concentration | Number plants | Azoxystrobin | Sampangin |
|---|---|---|---|
| 0 | 45 | 22.34 | 22.34 |
| 625 | 36 | 4.46 | 8.31 |
| 1250 | 36 | 1.58 | 1.26 |
| 2500 | 36 | 3.54 | 0.80 |

[a]Disease severity scores (# disease lesions) of detached strawberry leaves following inoculation with Collectotrichum fragariae and treatment with four concentrations of commercial or experimental fungicide.

We claim:

1. A method for limiting the pathological conditions in plants resulting from a fungal organism comprising delivering into the environment of said plants in a fungicidally effective concentration a compound having the formula:

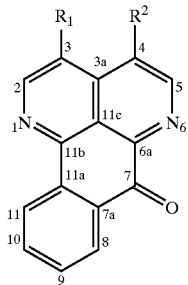

wherein $R_1$ is selected from the group consisting of H and an alkoxy group having 1 to 6 carbon atoms; $R_2$ is H, Br, Cl, F or I, or $R_2$ is an alkoxy group having 1 to 6 carbon atoms when $R_1$ is H, or $R_2$ is a benzo group at the 4–5 positions when $R_1$ is H.

2. The method of claim 1 wherein said fungal organism is *Colletotrichum fragariae*.

3. The method of claim 1 wherein said fungal organism is *Colletotrichum acutatum*.

4. The method of claim 1 wherein said fungal organism is *Colletotrichum gloeosporiodes*.

5. The method of claim 1 wherein said fungal organism is *Botrytis cinerea*.

6. The method of claim 1 wherein said fungal organism is *Fusarium oxysporum*.

7. The method of claim 1 wherein said delivering of said compound is in a composition comprising an aqueous non-phytotoxic carrier acceptable to plant use and a surface active agent to make the compound more soluble in said aqueous carrier.

8. The method of claim 1 wherein said compound is selected from the group consisting of sampangine, 3-methoxysampangine, 4-methoxysampangine, 4-bromosampangine, and 4,5-benzosampangine.

* * * * *